(12) United States Patent
Wang et al.

(10) Patent No.: US 11,846,280 B2
(45) Date of Patent: Dec. 19, 2023

(54) FLUSHING PUMP

(71) Applicant: Keymed (Medical & Industrial Equipment) Limited, Southend-on-Sea (GB)

(72) Inventors: Chu Wang, Southend-on-Sea (GB); Simon Morrison, Southend-on-Sea (GB); Gareth Sykes, Southend-on-Sea (GB)

(73) Assignee: KEYMED (MEDICAL & INDUSTRIAL EQUIPMENT) LIMITED, Southend-on-the-Sea (GB)

( * ) Notice: Subject to any disclaimer, the term of this patent is extended or adjusted under 35 U.S.C. 154(b) by 116 days.

(21) Appl. No.: 17/583,327

(22) Filed: Jan. 25, 2022

(65) Prior Publication Data

US 2022/0236749 A1 Jul. 28, 2022

(30) Foreign Application Priority Data

Jan. 25, 2021 (GB) ...................................... 2100984

(51) Int. Cl.
*F04B 51/00* (2006.01)
*F04B 43/00* (2006.01)
(Continued)

(52) U.S. Cl.
CPC .............. *F04B 51/00* (2013.01); *F04B 49/10* (2013.01); *A61M 2209/02* (2013.01); *F04B 23/02* (2013.01); *F04B 43/0081* (2013.01)

(58) Field of Classification Search
CPC ........ F04B 23/02; F04B 17/03; F04B 49/065; F04B 49/10; F04B 51/00; A61M 2209/02
See application file for complete search history.

(56) References Cited

U.S. PATENT DOCUMENTS 11,323,285 B1 * 5/2022 Bryant ..................... G01V 3/02
2003/0097232 A1 5/2003 McClendon et al.
(Continued)

FOREIGN PATENT DOCUMENTS

CN 209069676 U * 7/2019
EP 3 088 021 A1 11/2016
(Continued)

OTHER PUBLICATIONS

Extended European Search Report dated Apr. 25, 2022 received in 21209066.6.
(Continued)

*Primary Examiner* — Charles G Freay
(74) *Attorney, Agent, or Firm* — Scully, Scott, Murphy & Presser, P.C.

(57) ABSTRACT

A flushing pump including: a pump configured to draw fluid from a reservoir and expel the drawn fluid from a fluid outlet; a processor configured to control operation of the pump; and a remote controller connection port in electrical communication with the processor. The remote controller connection port including: an output system connection point; an input system connection point; a debugging connection point; and a ground connection point held at a reference voltage level. Wherein the processor is configured to output diagnostic information to the output system connection point in response to the debugging connection point receiving a signal at the reference voltage level.

15 Claims, 2 Drawing Sheets

(51) Int. Cl.
    *F04B 49/10*     (2006.01)
    *F04B 23/02*     (2006.01)

(56) References Cited

U.S. PATENT DOCUMENTS

2013/0214793 A1*   8/2013   Troxler ................... F04B 51/00
                                                                        324/537
2013/0267779 A1   10/2013   Woolford et al.
2016/0153443 A1*   6/2016   Glass ...................... F04B 51/00
                                                                         417/63

FOREIGN PATENT DOCUMENTS

EP         3 543 531 A1     9/2019
WO     2018/211259 A1   11/2018

OTHER PUBLICATIONS

Great Britain Search Report dated Jun. 21, 2021 received in GB2100984.0.

* cited by examiner

FLUSHING PUMP

CROSS-REFERENCE TO RELATED APPLICATION

The present application is based upon and claims the benefit of priority from GB 2100984.0 filed on Jan. 25, 2021, the entire contents of which is incorporated herein by reference.

BACKGROUND

Field

The present disclosure relates generally to flushing pumps, such as those for use during endoscopic surgery.

Prior Art

Flushing pumps are used to provide a supply of liquid to a medical instrument, for flushing and irrigation, during medical procedures such as endoscopies. Generally sterile water is drawn from a reservoir and is pumped to a remote output which is used to flush and irrigate the region of interest during the surgery. The flushing pump may include two pumps (one for supplying liquid under pressure, and another for providing suction), or a single pump may facilitate both functions. For example, peristaltic pumps may be used as the flushing pump to avoid contact between mechanical parts and the sterile flushing water. Examples of flushing pumps are described in WO 2018 211259 A1 and EP 3 543 531 A1.

With existing flushing pumps, it is not possible to evaluate its usage and performance, in order to carry out any useful diagnostics regarding the flushing pump. Thus, the entire flushing pump must be removed from service and disassembled so that it can be inspected. There is therefore a need for an improved flushing pump.

SUMMARY

Accordingly, a flushing pump is provided. The flushing pump comprising: a pump for drawing fluid from a reservoir and expelling the drawn fluid from a fluid outlet; a processor configured to control operation of the pump; a remote controller connection port in electrical communication with the processor, the remote controller connection port comprising: an output system connection point; an input system connection point; a debugging connection point; and a ground connection point held at a reference voltage level, wherein the processor is configured to output diagnostic information to the output system connection point in response to the debugging connection point receiving a signal at the reference voltage level. This allows for remote diagnostics and servicing.

The reference voltage level may be an earth ground voltage. This is a convenient reference voltage, which may also be used by a remote controller attached to the connection port.

The flushing pump may further comprise: a remote controller comprising a remote controller connector for attachment to the connection port, the remote controller being configured to transmit a control signal to the input system connection point to instruct the processor to operate the flushing pump. The remote controller allows the user to remotely operate the flushing pump, such as by starting and/or stopping pumping.

The remote controller connector may be configured to leave the debugging connection point at a floating voltage. Left at a floating voltage, the processor will not enter the debugging mode where diagnostic information is output. This may be achieved by having nothing connected to the debugging connection point.

The flushing pump may further comprise: a debugging cable comprising a debugging connector for attachment to the connection port, the debugging connector being configured to provide the reference voltage level to the debugging connection point. This provides a debugging method by attaching the correct cable, which may be provided to service providers.

The debugging connector may comprise an electrical connection configured to connect the debugging connection point and the ground connection point when the debugging connector is inserted into the connection port. This provides a hard-wired solution to enter the debugging mode using existing connection points.

The debugging connector may further comprise a serial output. The debugging connector may further comprise a serial-to-USB adaptor. This provides an output format for the diagnostic information.

Each connection point may be a socket. For example, a plug connector or female connector. It may be more convenient to insert the external component (i.e., the diagnostic cable or remote controller) into a socket, rather than the other way around.

The connection port may be suitable for receiving a four-pin connector. The four-pin connector may be a Hirose four-pin connector. Four pin connectors are resilient and effective connectors for such a flushing pump.

The processor may be further configured to perform a handshake process in response to the debugging connection point receiving a signal at the reference voltage level, before outputting diagnostic information. This provides a software check, in addition to the hardware check of the debugging connection point. This provides a further layer of security and prevents unauthorized users from inadvertently triggering the processor to enter the debugging mode and outputting diagnostic information.

The pump may be a peristaltic pump. This prevents contact between the fluid and the mechanical parts of the pump, thereby reducing the risk of any contamination.

The present disclosure further provides a method of servicing a flushing pump, the method comprising: providing a flushing pump having features discussed above; attaching a debugging cable to the connection port to provide the reference voltage level to the debugging connection point; and reviewing the diagnostic information output from the flushing pump. This method allows servicing of the flushing pump using the architecture discussed in the present specification.

BRIEF DESCRIPTION OF THE DRAWINGS

The present disclosure refers, by way of example only, to the accompanying Figures in which.

DETAILED DESCRIPTION

Figure 1:
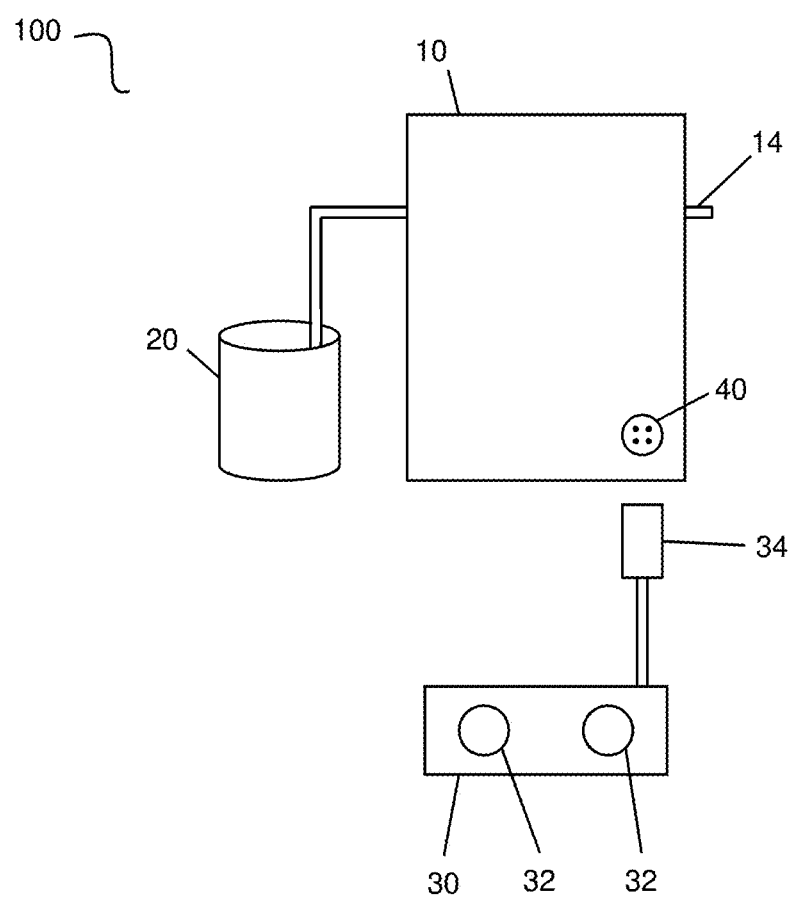
FIG. 1 illustrates a schematic of a flushing pump including a remote controller connection port.

FIG. 1 shows a schematic of a flushing pump 100. The flushing pump 100 includes a pump 10. The pump 10 may be any suitable form of pump. In an embodiment, the pump 10 may be a peristaltic pump (also known as a roller pump) such that the mechanical elements of the pump 10 do not contact the fluid being pumped. In a peristaltic pump, fluid is contained within a flexible tube fitted inside a cavity within a pump casing. A rotor with a number of pressing elements attached to the external circumference of the rotor progressively compresses the flexible tube. As the rotor turns, the part of the tube under compression is pinched closed, thus forcing the fluid to be pumped to move through the flexible tube. Additionally, as the tube opens to its natural state after the passing of the pressing element, fluid flow is induced to the peristaltic pump.

The pump 10 is configured to draw fluid from a reservoir 20, such as a water supply or container. The fluid may be a sterile fluid such as sterile water. This fluid is drawn from the reservoir 20 by the pump 10. The drawn fluid is then expelled from a fluid outlet 14 of the pump 10. The fluid outlet 14 may be a connection point for attaching a flexible tube thereto. The flexible tube may be positionable within a patient's body at a site which is to be irrigated. When the pump 10 operates, fluid is drawn from the reservoir 20 and delivered to the fluid outlet 14 and then on to the area to be irrigated.

The pump 10 includes a processor 16 (not shown in FIG. 1), such as a CPU or computer, which controls operation of the pump 10. This may include, for example, starting and/or stopping pump 10 operation, controlling the rate of pumping, and/or any other relevant control of the pump 10. The pump 10 further comprises a remote controller connection port 40. The remote controller connection port 40 is in electrical communication with the processor 16.

A remote controller 30 is connectable to the remote controller connection port 40. The remote controller 30 may include a remote controller connector 34 which is attachable to the remote controller connection port 40. For example, the remote controller connector 34 may be insertable into the remote controller connection port 40. That is, the remote controller connector 34 may be a male connector (also known as a pin connector) and the remote controller connection port 40 may be a female connector (also known as a plug connector or a socket connector). Of course, this may be reversed without departing from the present disclosure.

With the remote controller connector 34 connected to the remote controller connection port 40, the remote controller 30 is in electrical communication with the processor 16. This allows the remote controller 30 to send commands to the processor 16 to control operation of the pump 10. For example, the remote controller 30 may comprise one or more buttons 32 which control operation of the pump 10. In an embodiment, the remote controller 30 may control starting and stopping of the pump 10. The remote controller may be actuated via any suitable mechanism, but in an embodiment it may take the form of a switch, such as a foot pedal operated by the user's feet.

Typically, the remote controller 30 will be arranged near a video monitor which the user is using to view the output from a camera being used in the procedure (such as endoscopy).

Figure 2:
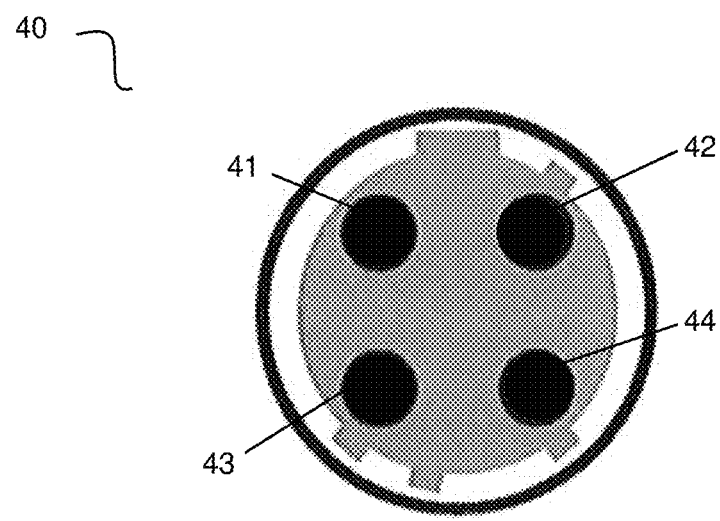
FIG. 2 illustrates a schematic of the remote controller connection port of FIG. 1.

A schematic of the remote controller connection port 40 is shown in FIG. 2. While this Figure shows an embodiment of a circular four-pin connector, the remote controller connection port 40 may be any suitable connector. In an embodiment, the remote controller connection port 40 may be a port configured to receive a Hirose four-pin connector.

Figure 3:
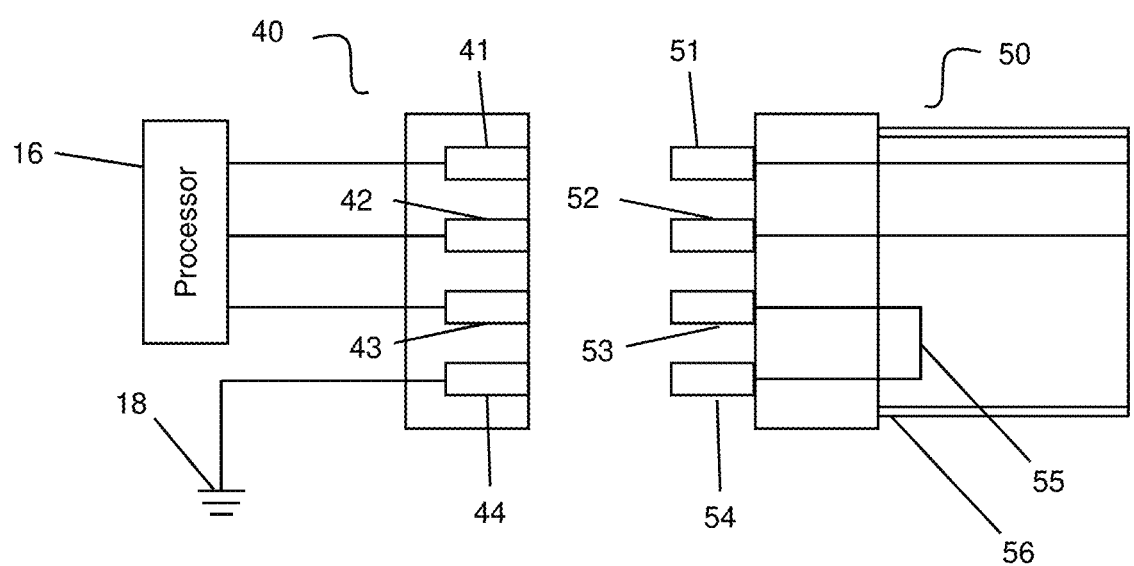
FIG. 3 illustrates a schematic circuit diagram of a remote controller connection port and a remote controller connector.

The remote controller connection port 40 includes a number of connection points. These connection points may be pins (i.e., elongate elements extending from a face of the remote controller connection port 40, suitable for receipt in corresponding plugs) or plugs (i.e., cavities formed in a face of the remote controller connection port 40, suitable for receiving corresponding pins), or any other suitable mechanism. The wiring of the connection ports is best shown in FIG. 3. While the depicted embodiment includes four connection points, it is noted that any suitable number of connection points may be used. For example, additional connection points may be provided to increase functionality. Alternatively, or additionally, one or more of the connection points may be combined.

The connection points include an output system connection point 41 and an input system connection point 42. When the remote controller 30 is connected, these two system connection points 41, 42 may be used to send and receive signals to and from the remote controller 30 to allow the remote controller 30 to control operation of the pump 10. These system connection points 41, 42 may be in electrical communication with the processor 16 such that system information can be sent to and from the processor 16. The remote controller 30 may transmit a control signal to the input system connection point 42, which is then transmitted to the processor 16 to instruct the processor to operate the pump 10 and hence the flushing pump 100.

A ground connection point 44 is provided, which is held at a reference voltage level. This reference voltage level may be an earth ground voltage, supplied via an earth connection 18. The ground connection point 44 may be directly connected to the reference voltage as shown in FIG. 3. Alternatively, the ground connection point 44 may connect to the processor 16 or other intermediary component. When the remote controller 30 is connected to the remote controller connection port 40, the ground connection point 44 may provide the reference voltage to the remote controller 30.

A debugging connection point 43 is provided. The debugging connection point 42 is electrically connected to the processor 16. When the processor 16 receives a signal at the reference voltage level from the debugging connection point 43, the processor 16 enters a diagnostic mode. In this diagnostic mode, the processor 16 may output diagnostic information via the output system connection point 41. When the remote controller 30 is connected, the debugging connection point 43 may be left floating. That is, the remote controller connector 34 may not have any electrical connection for the debugging connection point 43. As this leaves the debugging connection point 43 floating, the processor 16 does not enter the diagnostic mode.

The flushing pump 100 may further comprise a debugging cable 56. The debugging cable may be used to perform diagnostics of the flushing pump 100. The debugging cable may comprise a debugging connector 50, which is connectable to the remote controller connection port 40. Thus, the debugging connector 50 may be generally the same physical form as the remote controller connector 34.

The debugging connector 50 is configured to provide the reference voltage level to the debugging connection port 43. For example, the debugging connector 50 may include an electrical connection 55 connecting the debugging connection port 43 to the ground connection point 44. This therefore acts as a hard-wired link between the two ports when the debugging connector 50 is connected to the remote controller connection port 40.

With the debugging connector 50 connected to the remote controller connection port 40, the reference voltage is provided to the processor 16 from the debugging connection point 43 and hence the processor 16 enters the debugging mode.

The debugging cable is configured to connect at its other end to a debugging system, such as a terminal or computer. For example, the debugging cable may include a serial output. This could be, for example, in the form of a serial-to-USB adaptor such that the debugging cable can be plugged into a USB port.

With the debugging cable connected to the debugging system, the processor 16 may perform a handshaking process to establish a connection with the debugging system. This may include one or more of the steps of verifying the connection, determining the speed, or authorizing the connection. For example, the debugging system may need to transmit a password to the processor 16 before any diagnostic information is output from the processor 16.

When the processor 16 outputs diagnostic information, this may be via the output system connection point 41. This diagnostic information may be transferred to the debugging system, for further processing and analysis. This diagnostic information may then be reviewed and used to service the flushing pump 100. The diagnostic information may be any information regarding the operation of the flushing pump 100. This may include, but is not limited to, usage durations, usage speeds, time between usage, usage durations at particular speeds, error messaging.

The user may input a request for particular diagnostic information into the debugging system. This can be transmitted to the system input connection point 42 and thereby transmitted to the processor 16. The processor 16 will then receive this request and output the appropriate diagnostic information via the system output connection point 41.

All of this diagnostic information can then be reviewed, either automatically or by human input, and used to determine appropriate servicing required for the flushing pump 100. The diagnostic information may be analysed to determine which procedures the flushing pump 100 has been used for. For example, a particular characteristic usage profile may indicate that a particular procedure has been carried out. In a surgical procedure, as an example, the speed of the flushing pump 100 is likely to be low, but it will be used at this low speed for a long duration.

Thus, a method of servicing the flushing pump 100 is provided. A debugging cable is attached to the remote controller connection port 40. The debugging cable is configured to provide the reference voltage level to the debugging connection point 43. This then triggers the processor 16 to enter the debugging mode and output diagnostic information. As noted above, the processor 16 may first carry out a handshaking step to verify that the diagnostic information should be output. Finally, the diagnostic information may be used to evaluate the flushing pump 100. For example, by reviewing the diagnostic information output from the flushing pump 100.

This method of servicing the flushing pump 100 may indicate to a maintenance team which components require repair and/or replacement, thereby prolonging the life of the flushing pump 100.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A flushing pump comprising:
   a pump configured to draw fluid from a reservoir and expel the drawn fluid from a fluid outlet;
   a processor configured to control operation of the pump; and
   a remote controller connection port in electrical communication with the processor, the remote controller connection port comprising:
   an output system connection point;
   an input system connection point;
   a debugging connection point; and
   a ground connection point held at a reference voltage level,
   wherein the processor is configured to output diagnostic information to the output system connection point in response to the debugging connection point receiving a signal at the reference voltage level.

2. The flushing pump of claim 1, wherein the reference voltage level is an earth ground voltage.

3. A flushing pump system comprising:
   the flushing pump of claim 1; and
   a remote controller comprising a remote controller connector configured to be connected to the remote controller connection port, the remote controller being configured to transmit a control signal to the input system connection point to instruct the processor to operate the flushing pump when the remote controller connector is connected to the remote controller connection port.

4. The flushing pump system of claim 3, wherein the remote controller connector is configured to leave the debugging connection point at a floating voltage.

5. A flushing pump system comprising:
   the flushing pump of claim 1; and
   a debugging cable comprising a debugging connector for connection to the remote controller connection port, the debugging connector being configured to provide the reference voltage level to the debugging connection point.

6. The flushing pump system of claim 5, wherein the debugging connector comprises an electrical connection configured to connect the debugging connection point and the ground connection point when the debugging connector is connected to the remote controller connection port.

7. The flushing pump system of claim 5, wherein the debugging connector further comprises a serial output.

8. The flushing pump system of claim 7, wherein the debugging connector further comprises a serial-to-USB adaptor.

9. The flushing pump of claim 1, wherein each of the output system connection point, input system connection point, debugging system connection point and ground connection point is a socket.

10. The flushing pump of claim 1, wherein the remote controller connection port is configured to receive a four-pin connector.

11. The flushing pump of claim 10, wherein the four-pin connector is a Hirose four-pin connector.

12. The flushing pump of claim 1, wherein the processor is further configured to:
    output diagnostic information for the pump; and prior to outputting the diagnostic information, perform a handshake process in response to the debugging connection point receiving a signal at the reference voltage level.

13. The flushing pump of claim 1, wherein the pump is a peristaltic pump.

14. A method of servicing a pump configured to draw fluid from a reservoir and expel the drawn fluid from a fluid outlet, wherein the pump comprises a processor for controlling operation of the pump and a remote controller connection port in communication with the processor, the method comprising:
- attaching a debugging cable to the remote controller connection port to provide a reference voltage level to a debugging connection point provided on the remote controller connection port;
- outputting diagnostic information from the processor in response to the reference voltage level; and
- reviewing the diagnostic information output from the processor.

15. A control system comprising a processor configured to:
- control an operation of a pump configured to draw fluid from a reservoir and expel the drawn fluid from a fluid outlet;
- receive an input from a remote controller connector removably connected to the processor;
- diagnose the pump in response to the remote controller connector receiving a signal at a reference voltage level; and
- output a diagnosis of the pump to the remote controller connector.

* * * * *